United States Patent [19]

Cassar et al.

[11] 4,128,572

[45] Dec. 5, 1978

[54] PROCESS FOR PREPARING PHENYLACETIC ACID

[75] Inventors: Luigi Cassar; Marco Foá, both of Novara, Italy

[73] Assignee: Montedison S.p.A., Milan, Italy

[21] Appl. No.: 870,324

[22] Filed: Jan. 18, 1978

[30] Foreign Application Priority Data

Jan. 18, 1977 [IT] Italy .................... 19389 A/77

[51] Int. Cl.$^2$ .................... C07C 51/00; C07C 63/54
[52] U.S. Cl. .................................... 562/406
[58] Field of Search .................... 260/515 A, 515 R

[56] References Cited

U.S. PATENT DOCUMENTS

| | | | |
|---|---|---|---|
| 3,116,306 | 12/1963 | Heck | 260/410.9 |
| 3,708,529 | 1/1973 | Cassar et al. | 260/515 R |
| 3,928,429 | 12/1975 | El-Chahowi et al. | 260/515 R |
| 4,034,004 | 7/1977 | Cassar et al. | 260/515 R |

FOREIGN PATENT DOCUMENTS 1245029  9/1971  United Kingdom.

OTHER PUBLICATIONS

Organic Syntheses, Collective, vol. I, pp. 107–109.

*Primary Examiner*—Jane S. Myers
*Attorney, Agent, or Firm*—Morgan, Finnegan, Pine, Foley & Lee

[57] ABSTRACT

This invention relates to a process for preparing phenylacetic acid. In particular, the present invention relates to a catalytic process for the synthesis of the alkaline salts of phenylacetic acid by carbonylation of benzyl halides in a diphase system in the presence of cobalt carbonyl complexes. More particularly, the present invention relates to a process for preparing alkaline salts of phenylacetic acid by reacting a benzyl halide selected from chloride and bromide with carbon monoxide in the presence of a catalyst consisting in a salt of cobalt hydrocarbonyl, characterized in that the reaction is conducted in an aqueous/organic diphase system consisting of (a) an aqueous solution of an inorganic alkaline base, and (b) the benzyl halide in an organic solvent, in the presence of a catalyst system composed by a quaternary alkylammonium salt and by a cobalt hydrocarbonyl salt, at atmospheric pressure and at a temperature ranging from 20° to 70° C about.

10 Claims, No Drawings

PROCESS FOR PREPARING PHENYLACETIC ACID

BACKGROUND OF THE INVENTION

Phenylacetic acid can be easily prepared from alkaline salts by acidification etc. according to widely conventional techniques.

Phenylacetic acid is known compound having many applicative possibilities in the industry.

Phenylacetic acid may be considered as an important intermediate for the preparation of perfumes (phenylethyl phenyl acetate, benzyl phenylacetate, etc.) and in the field of pesticides, such as the ethyl ester of the dimethyl-dithiophosphoryl-phenylacetic acid known under the trade name Cidial, etc.

Several methods of synthetising phenylacetic acid are therefore known. For example, phenylacetic acid may be prepared by reacting benzyl chloride with alkaline cyanides and by successively saponifying the obtained nitrile to phenylacetic acid. Such method comprises more than one step, further complicated by the use of reagents such as cyanides difficult to handle, and involving operative risks and possible environmental pollutions, also because of the simultaneous formation of ammonium sulphate as by-product. The industry's interest in the aforesaid method is therefore rather sparing.

Phenylacetic acid is also obtainable, according to other methods described in the literature, by carbonylation of benzyl halides in an alkaline medium in the presence of catalyst systems based on metal-carbonyl complexes of Ni, Co.

Finally, it is also known how to prepare esters of phenylacetic acid by carbonylation of benzyl chloride in the presence of a catalyst system based on salts of cobalt hydrocarbonyl in hydroalcoholic solvents.

These methods, however, exhibit various drawbacks residing predominantly in the use of high pressures, in the necessity of preparing the catalyst separately, in the unsatisfactory reaction yields and rates, in the use of special solvents, and so on. These drawbacks, substantially, badly affect such methods for the purposes of the industrial applications thereof.

OBJECTS OF THE INVENTION

Thus it is an object of the present invention to provide a simple and economic process for industrially preparing phenylacetic acid, free from the drawbacks cited in connection with the prior art taken into examination.

The process forming the object of the present invention permits to obviate the disadvantages of the prior art by having recourse to the synthesis of phenylacetic acid from carbon monoxide and benzyl halides catalyzed by cobalt carbonyl complexes in an aqueous alkaline-organic diphase system.

Other objects of the invention will be apparent from the discussion which follows:

SUMMARY OF THE INVENTION

A process for preparing alkaline salts of phenylacetic acid by reacting a benzyl halide selected from chloride and bromide with carbon monoxide in the presence of a catalyst consisting in a salt of cobalt hydrocarbonyl, characterized in that the reaction is conducted in an aqueous/organic diphase system consisting of a) an aqueous solution of an inorganic alkaline base, and b) the benzyl halide in an organic solvent, in the presence of a catalyst system composed by a quaternary alkylammonium salt and by a cobalt hydrocarbonyl salt, at atmospheric pressure and at a temperature ranging from 20° to 70° C about.

GENERAL DESCRIPTION OF THE INVENTION

It has been found that the objects of this invention may be realized by a process for preparing alkaline salts of phenylacetic acid by reaction of a benzyl halide, selected from chloride and bromide, with a carbon monoxide in the presence of a catalyst consisting in a salt of cobalt hydrocarbonyl, characterized in that the reaction is conducted in an aqueous/organic diphase system composed by (a) an aqueous solution of an inorganic alkaline base, and (b) the benzyl halide in an organic solvent, in the presence of a catalytic system composed by a quaternary alkylammonium salt and by a cobalt hydrocarbonyl salt, at atmospheric pressure and at temprtures ranging from about 20° C to 70° C.

The reaction can be schematically represented by the following equation:

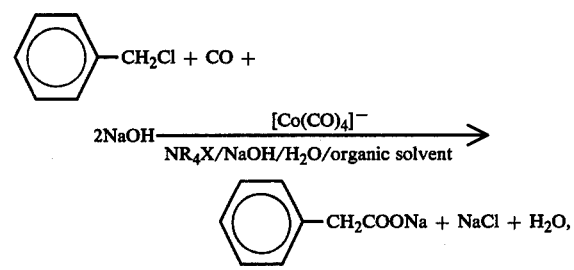

wherein $NR_4X$ indicates the salt (halide) of alkylammonium, as better defined hereinafter. From the alkaline phenylacetate the corresponding acid is obtained by acidification with mineral acids (HCl, $H_2SO_4$) according to conventional techniques.

The reaction, as explained hereinabove, is characterized in that it is conducted in an aqueous/organic diphase system, whose organic phase consists in the benzyl halide, selected from chloride and bromide, in solution in an organic solvent, selected from amongst aromatic hydrocarbons, aromatic and aliphatic ethers and aromatic halogen-derivatives; while the aqueous phase consists in an aqueous solution of an inorganic base selected from NaOH and KOH and containing also a quaternary alkyl-ammonium salt of formula $NR_4X$, wherein R is an alkyl radical containing 1 to 20 carbon atoms and X is a halogen such as chlorine, bromine, iodine.

The organic solvent is preferably selected from among diphenyl ether, diisopropyl ether, p-xylene, o-dichlorobenzene, benzene, etc.

The catalyst is composed of salts of cobalt hydrocarbonyl, preferably of sodium salt $Na[Co(CO)_4]$.

it is possible to prepare "in situ" the above said sodium salt by introducing into the reaction medium cobalt carbonyl $Co_2(CO)_8$ which, under the reaction conditions, in the presence of the organic base NaOH, provides the corresponding cobalt salt $Na[Co(CO)_4]$.

The abovesaid cobalt compounds are known per se and available on the market. In any case they are prepared according to conventional techniques; for example $Co_2(CO)_8$ is prepared from $CoCO_3$ and CO under a hydrogen pressure in petroleum ether. Na[Co(CO)$_4$] is prepared, in its turn, by reduction of Co$_2$(CO)$_8$ with a 1% sodium amalgam in tetrahydrofuran.

The reaction is concluded in a time generally comprised between 1 and 24 hours approximately, depending on the conditions of temperature, concentration, employed catalyst, etc.

The inorganic base, selected from NaOH and KOH, is introduced in the form of an aqueous solution preferably at a concentration ranging from 5% to 50% by weight, and in molar amounts in excess in respect of the stoichiometric benzyl chloride, i. e. : the benzyl chloride : NaOH molar ratio is higher than 1:2, without being critical.

The catalyst based on cobalt carbonyl or on (sodium) salt of cobalt hydrocarbonyl is added in catalytical amounts; profitable amounts are obtained with a benzyl halide : cobalt catalyst molar ratio comprised between 10:1 and 200:1.

The quaternary alkyl-ammonium salt is introduced in an equimolar ratio in respect of the cobalt catalyst, or even in a higher ratio, preferably ranging from 1:1 to 4:1.

Some preferred quaternary alkyl-ammonium salt are benzyl-trimethyl-ammonium chloride, benzyl-triethyl-ammonium chloride, tetrabutyl-ammonium bromide, etc.

Benzyl halide is finally introduced gradually into the reaction mass.

An effective embodiment of the process is the following.

The solvent, the alkaline solution (NaOH), containing also the quaternary alkyl-ammonium salt, the benzyl halide (chloride) and the cobalt catalyst are introduced, in a CO atmosphere, under ambient pressure, into a reactor equipped with a stirrer and a temperature regulating system.

Benzyl halide is introduced gradually for the purpose of best regulating the reaction. The mixture is then brought to the desired temperature and kept under a CO head until completion of the reaction, i.e. until conclusion of the CO absorption.

The following operations are then carried out : separation of the aqueous phase containing the alkaline salt of phenylacetic acid in solution, such separation being effectible also continuously; acidification of the aqueous phase with concentrated sulphuric or hydrochloric acid, and extraction of the obtained phenylacetic acid with a solvent (ethyl ether), according to conventional methods. The organic phase is directly recycled for a successive carbonylation, without any necessity of recovering the catalyst, thanks to the diphase technique of the reaction.

Depending on the alkali (NaOH) concentration, alkaline salt of phenylacetic acid may also come, in part or in whole, in the form of a precipitate, that is filtered, dissolved in H$_2$O, acidified, etc.

As compared with the prior art, the process offers several advantages, that may be summarized as follows :

(1) It is possible to employ aqueous solutions of NaOH or KOH without having to check the amount or the pH, as in such diphase system the hydrolysis reaction of benzyl halide to benzyl alcohol is extremely slow.
(2) The sodium or potassium phenyl acetate that has formed passes to the aqueous phase and can be easily separated by filtration or centrifugation after having allowed it to crystallize.
(3) By choosing a suitable ammonium salt it is possible to maintain the cobalt catalyst thoroughly dissolved in the organic phase, wherefore it is easy te separate the aqueous phase containing the alkaline phenyl acetate and to recycle the organic solution containing the catalyst, thus realizing a continuous process.

SPECIFIC DESCRIPTION OF THE INVENTION

The process will be now described more in detail in the following examples, which are given, however, for merely illustrative purposes.

The possibility of recycling the organic and aqueous phases is exemplified in example 7.

EXAMPLE 1

Into a 250-cc flask, equipped with a stirrer, a thermometer, a water-cooler and a dropping funnel, there were introduced, under a CO head :

| | | |
|---|---|---|
| NaOH aqueous solution at 40% | 50 | cc |
| diphenyl ether | 15 | cc |
| benzyl-trimethyl-ammonium chloride | 1 | g |
| Na[Co(CO)$_2$] | 0.5 | g |

Keeping a temperature of 55°–56° C, 16.5 g of benzyl chloride were dropped thereinto in 1 hour. The reaction mixture was stirred for further 2 hours, until conclusion of the CO absorption.

The raw reaction mixture was diluted with water an HCl and extracted with ethyl ether.

A sample was esterified with diazomethane and subjected to gas-chromatographic analysis.

Such analysis revealed that the phenylacetic acid yield was equal to 84.7% calculated on the benzyl chloride introduced.

EXAMPLE 2

Into the apparatus described in example 1 and following the same modalities, the following was introduced:

| | | |
|---|---|---|
| NaOH aqueous solution at 40% | 50 | cc |
| diisopropyl ether | 15 | cc |
| benzyl-trimethyl-ammonium chloride | 1 | g |
| Na[Co(CO)$_4$] | 0.5 | g |

Following the modalities of the preceding example, 16.5 g of benzyl chloride were added, whereupon it was operated as in example 1.

The raw reaction mixture, after esterification with diazomethane, was subjected to a gas-chromatographic analysis, that revealed a phenylacetic acid yield of 70.5% calculated on the benzyl chloride introduced.

EXAMPLE 3

Into the apparatus described in example 1 and following the same modalities, there were introduced:

| | | |
|---|---|---|
| NaOH aqueous solution at 40% | 50 | cc |
| p-xylene | 15 | cc |
| benzyl-trimethyl-ammonium chloride | 1 | g |
| Na[Co(CO)$_4$]0.5 | | g |

Following the modalities of example 1, 16.5 g of benzyl chloride were introduced. It was then operated conforming to example 1, and the gas-chromatographic analysis revealed a phenylacetic acid yield of 74.6% calculated on the fed benzyl chloride.

EXAMPLE 4

Into the apparatus described in example 1 and following the same modalities, there were introduced:

| | | |
|---|---|---|
| NaOH aqueous solution at 40% | 70 | cc |
| o-dichlorobenzene | 30 | cc |
| benzyl-trimethyl-ammonium chloride | 1 | g |
| Na[Co(CO)$_4$] | 0.5 | g |

Following the modalities of example 1, 16.5 g of benzyl chloride were introduced. It was then operated as in example 1, and the gas-chromatographic analysis revealed a phenylacetic acid yield of 74% calculated on the fed benzyl chloride.

EXAMPLE 5

Into a 50-cc flask, equipped with a water-cooler, a thermometer and a magnetic stirrer, under a CO head, there were introduced:

| | | |
|---|---|---|
| NaOH aqueous solution at 10% | 15 | cc |
| Na[Co(CO)$_4$] | 100 | mg |
| benzyl-trimethyl-ammonium chloride | 300 | mg |
| benzene | 1 | cc |

Keeping a temperature of 25° C, 1.38 g of benzyl bromide were added in 2.5 hours.

At the conclusion of such addition it was stirred for further 0.5 hours.

A sample was drawn and, after acidification, extraction with ethyl ether and esterification with diazomethane, it was subjected to gas-chromatographic analysis.

From such gas-chromatographic analysis it resulted a practically quantitative yield of phenylacetic acid.

EXAMPLE 6

Into the apparatus described in example 5 and following the same modalities, there were introduced:

| | | |
|---|---|---|
| NaOH aqueous solution at 7% | 15 | cc |
| Co$_2$(CO)$_8$ | 307 | mg |
| benzyl-trimethyl-ammonium chloride | 370 | mg |
| benzene | 2 | cc |

Keeping a temperature of 25° C, 1.38 g of benzyl bromide were added in 3.5 hours.

At the conclusion of such addition, stirring was continued for 4.5 hours. A sample was drawn and, after acidification, extraction with ethyl ether and esterification with diazomethane, it was subjected to gas-chromatographic analysis. Such gas-chromatographic analysis revealed a phenylacetic acid yield of 87% calculated on the fed benzyl bromide.

EXAMPLE 7

Into the same apparatus of example 1 and according to the same modalities, there were introduced, under a CO head :

| | | |
|---|---|---|
| NaOH aqueous solution at 40% saturated with phenylacetic acid coming from a preceding cycle | 50 | cc |

-continued

| | | |
|---|---|---|
| diphenyl ether | 15 | cc |
| benzyl-trimethyl-ammonium chloride | 1 | g |
| Na[Co(CO)$_4$] | 0.5 | g |

Keeping a temperature of 55°–56° C, 17.6 g of benzyl chloride were dropped in 1.5 hours.

The reaction mixture was stirred for further 2.5 hours until conclusion of the CO absorption.

The resulting suspension was filtered.

The filtrate, consisting of the aqueous and organic phases, could be recycled after addition of NaOH and optional restoring of the exhausted catalytic system. The solid residue was dissolved in water, the aqueous solution was acidified with concentrated HCl and extracted with ethyl ether. After evaporation of the ether, 16 g of phenylacetic acid were obtained, the yield being of 84.6% calculated on the benzyl chloride introduced.

What we claim is:

1. A process for preparing alkaline salts of phenylacetic acid by reacting a benzyl halide selected from chloride and bromide with carbon monoxide in the presence of a catalyst consisting in a salt of cobalt hydrocarbonyl, characterized in that the reaction is conducted in an aqueous/organic diphase system consisting of (a) an aqueous solution of an inorganic alkaline base and (b) the benzyl halide in an organic solvent, in the presence of a catalyst system composed by a quaternary alkyl-ammonium salt and by a cobalt hydrocarbonyl salt, at atmospheric pressure and at a temperature ranging from about 20° to 70° C.

2. A process according to claim 1, characterized in that the aqueous phase consists in an alkaline solution of an inorganic phase selected from NaOH and KOH, having a concentration ranging from 5% to 50% by weight.

3. A process according to claim 1, characterized in that the quaternary alkyl-ammonium salt is a halide having formula NR$_4$X, in which R is an alkyl radical containing up to 20 carbon atoms and X is chlorine, bromine, iodine.

4. A process according to claim 3, characterized in that the quaternary alkyl-ammonium salt is selected from amongst benzyl-trimethyl-ammonium chloride, benzyl-triethyl-ammonium chloride and tetrabutyl-ammonium bromide.

5. A process according to claim 1, characterized in that the catalyst is sodium tetracarbonyl cobaltate.

6. A process according to claim 1, characterized in that the solvent is selected from amongst aromatic hydrocarbons, aromatic and aliphatic ethers, aromatic halogen derivatives.

7. A process according to claim 6, characterized in that the solvent is selected from amongst diphenyl ether, diisopropyl ether, p-xylene, benzene and o-dichlorobenzene.

8. A process according to claim 1, characterized in that the organic base : benzyl halide molar ratio is higher than the reaction molar ratio.

9. A process according to claim 1, characterized in that the benzyl halide : cobalt catalyst molar ratio is comprised between 10:1 and 200:1.

10. A process according to claim 1, characterized in that the quaternary alkyl-ammonium salt : cobalt catalyst molar ratio is comprised between 1:1 and 4:1 approximately.

* * * * *